US008622548B2

(12) United States Patent  
Guo et al.

(10) Patent No.: US 8,622,548 B2
(45) Date of Patent: Jan. 7, 2014

(54) 3D RETINAL DISRUPTIONS DETECTION USING OPTICAL COHERENCE TOMOGRAPHY

(75) Inventors: Cheng-en Guo, Santa Clara, CA (US); Ben Jang, Cupertino, CA (US); Wenjing Li, Fremont, CA (US)

(73) Assignee: Optovue, Inc., Fremont, CA (US)

( * ) Notice: Subject to any disclaimer, the term of this patent is extended or adjusted under 35 U.S.C. 154(b) by 114 days.

(21) Appl. No.: 13/299,219

(22) Filed: Nov. 17, 2011

(65) Prior Publication Data

US 2012/0127427 A1 May 24, 2012

Related U.S. Application Data

(60) Provisional application No. 61/414,805, filed on Nov. 17, 2010.

(51) Int. Cl.
*A61B 3/14* (2006.01)
*A61B 3/00* (2006.01)

(52) U.S. Cl.
USPC .......................... 351/206; 351/210; 351/246

(58) Field of Classification Search
USPC ................................................. 351/200–246
See application file for complete search history.

(56) References Cited

U.S. PATENT DOCUMENTS

| 7,301,644 | B2 | 11/2007 | Knighton et al. ............. 356/479 |
| 7,480,058 | B2 | 1/2009 | Zhao et al. .................... 356/479 |
| 7,505,142 | B2 | 3/2009 | Knighton et al. ............. 356/479 |
| 7,744,221 | B2 | 6/2010 | Wei et al. ...................... 356/479 |
| 7,782,464 | B2 | 8/2010 | Mujat et al. | |
| 2007/0115481 | A1 | 5/2007 | Toth et al. | |
| 2007/0291277 | A1 | 12/2007 | Everett et al. | |
| 2008/0175465 | A1 | 7/2008 | Jiang et al. | |
| 2008/0187204 | A1 | 8/2008 | Reeves et al. | |
| 2009/0198094 | A1 | 8/2009 | Fenster et al. | |
| 2011/0103658 | A1* | 5/2011 | Davis et al. .................... 382/128 |
| 2011/0243415 | A1* | 10/2011 | Yonezawa et al. ............ 382/131 |
| 2012/0327368 | A1* | 12/2012 | Williams et al. ............... 351/221 |

FOREIGN PATENT DOCUMENTS

WO  WO-2010/071898 A2  6/2010
WO  WO-2010/080576 A1  7/2010

OTHER PUBLICATIONS

PCT International Search Report and the Written Opinion dated Mar. 20, 2012, in related International Appl. No. PCT/US2011/061252.
De Bruin et al., "In Vivo Three-Dimensional Imaging of Neovascular Age-Related Macular Degeneration Using Optical Frequency Domain Imaging at 1050 nm", *Investigative Ophthalmology & Visual Science*, Oct. 2008, vol. 49, No. 10, pp. 4545-4552.
Z. Yehoshua et al., "Comparison of Drusen Area Detected by Spectral Domain OCT and Color Fundus Photography", ARVO 2010, Presentation Abstract, Paper 2274, Apr. 3, 2013.

(Continued)

*Primary Examiner* — Mohammed Hasan
(74) *Attorney, Agent, or Firm* — Haynes and Boone, LLP (57) ABSTRACT

System and method for 3D retinal disruption/elevation detection, measurement and presentation using Optical Coherence Tomography (OCT) are provided. The present invention is capable of detecting and measuring the abnormal changes of retinal layers (retinal disruptions), caused by retinal diseases, such as hard drusen, soft drusen, Pigment Epithelium Detachment (PED), Choroidal Neovascularization (CNV), Geographic Atrophy (GA), intra retinal fluid space, and exudates etc. The presentations of the results are provided with quantitative measurements of disruptions in retina and can be used for diagnosis and treatment of retinal diseases.

26 Claims, 11 Drawing Sheets

(56) References Cited

OTHER PUBLICATIONS

S.R. Freeman et al., "Optical Coherence Tomography—Raster Scanning and Manual Segmentation in Determining Drusen Volume in Age-Related Macular Degeneration", Retina, Dec. 2009.

N. Jain et al., "Quantitative Comparison of Drusen Segmented on SD-OCT versus Drusen Delineated on Color Fundus Photographs", IOVS, vol. 51, No. 10, Oct. 2010.

K. Yi et al., "Spectral domain optical coherence tomography for quantitative evaluation of drusen and associated structural changes in non-neovascular age-related macular degeneration", Br J Ophthalmol., 93(2): 176-181, Feb. 2009.

S. Farsiu et al., "Fast Detection and Segmentation of Drusen in Retinal Optical Coherence Tomography Images", Proc. of Photonics West, San Jose, CA, Feb. 15, 2008.

J.A. Noble et al., "Ultrasound Image Segmentation: A Survey", IEEE Transactions on Medical Imaging, vol. 25, No. 8, pp. 987-1010, Apr. 15, 2006.

N. Otsu, "A Threshold Selection Method from Gray-Level Histograms", IEEE Transactions on Systems, Man, and Cybernetics, vol. 9, No. 1, pp. 62-66, 1979, Jun. 1, 1979.

L. Vincent et al., "Watersheds in Digital Spaces: an efficient algorithm based on immersion simulations", IEEE Transactions on Pattern Analysis and Machine Intelligence, vol. 13, No. 6, pp. 583-598, Jun. 1991.

Y. Cheng, "Mean shift, mode seeking and clustering", IEEE Transactions on Pattern Analysis and Machine Intelligence, vol. 17, No. 8, Aug. 1995.

R. Adams et al., "Seeded Region Growing", IEEE Transactions on Pattern Analysis and Machine Intelligence, vol. 16, pp. 641-647, Jun. 1994.

M. Szkulmowski et al., "Analysis of posterior retinal layers in spectral optical coherence tomography images of the normal retina and retinal pathologies", Journal of Biomedical Optics 12(4), Jul.-Aug. 2007.

R. Leitgeb et al., "Real-time measurement of in-vitro and in-vivo blood flow with Fourier domain optical coherence tomography", SPIE 5316, 226-232, Jul. 1, 2004.

M. Wojtkowski et al., "Real-time and static in vivo ophthalmic imaging by spectral optical coherence tomography", SPIE 5314, 126-131, Jul. 2004.

C. Hitzenberger et al., "Three-dimensional imaging of the human retina by high-speed optical coherence tomography", Optics Express, vol. 11, Issue 21, pp. 2753-2761, Oct. 20, 2003.

International Search Report and Written Opinion mailed Dec. 23, 2010, in International Application No. PCT/US2010/053603.

International Preliminary Report on Patentability mailed May 10, 2012, in International Application No. PCT/US2010/053603.

International Preliminary Report on Patentability mailed May 30, 2013, in related International Application No. PCT/US2011/061252.

\* cited by examiner

3D RETINAL DISRUPTIONS DETECTION USING OPTICAL COHERENCE TOMOGRAPHY

RELATED APPLICATIONS

This application claims priority to U.S. Provisional Application 61/414,805, filed on Nov. 17, 2010, which is herein incorporated by reference in its entirety.

BACKGROUND

1. Field of Invention

The embodiments described herein relates to methods and systems to detect and measure the retinal disruption/elevation of optical coherence tomography (OCT) data, as well as to present the detection and measurement results using 3D OCT data.

2. Background State of the Arts

Optical Coherence Tomography (OCT) has been an important modality for imaging eyes and facilitating ophthalmologists to diagnose and treat subjects with different eye diseases, retinal diseases in particular. The importance of OCT to the field of ophthalmology has also dramatically increased since Fourier Domain OCT (FD-OCT) became commercially available. FD-OCT has much higher scanning speed and higher resolution than the traditional Time Domain OCT (TD-OCT) technologies.

One of the major pathologic changes for retinal subjects is retinal layers disruption from their normal locations, especially around the Retinal Pigment Epithelium (RPE) and Photoreceptor Inner Segment/Outer Segment (PR-IS/OS) area. Quantitative measurements of such disruptions provide important information for ophthalmologists to diagnose and treat patients.

Previous methods using 3D OCT data follow the same scheme of first segmenting retinal layers, and then detecting the disruption (e.g. drusen) by comparing the segmented layers with expected referenced layers or with some layers which are elevated from the segmented layers by some constants. The referenced layers are often generated by fitting some smooth surfaces to the segmented layers, assuming the layers are not disrupted by any disease or pathology. In general, the presence of a disruption is determined by only comparing two 2D surfaces; this means the original 3D OCT data is not fully utilized after the layer segmentations have been performed. Such scheme has at least four major drawbacks. First, such detection methods are error prone because they are highly dependent on results of layer segmentations. If the 2D surface segmentation is not optimal, the disruption detection will be directly affected and likely produce inaccurate results. Second, to reduce noise effects associated with OCT data, layer segmentation often employs smoothing operation which can likely introduce the problem of scale. Excessive smoothing (such as the case with a large smoothing scale) will likely reduce details in desired features, while insufficient smoothing (with a small smoothing scale) will likely be inadequate to reduce noise effectively to generate optimal layer segmentations. Third, methods assuming constant elevations from segmented layers are less clinically meaningful because disruptions often occur locally with different and unpredictable sizes. Finally, a majority of existing methods only detect disruptions above the referenced layers, and any disruptions under the referenced layers are ignored. Since disruptions can occur above and below the reference layers of interest, it is important to devise a method to detect and measure disruptions in both scenarios.

SUMMARY

This Summary is provided to briefly indicate the nature and substance of the invention. It is submitted with the understanding that it will not be used to interpret or limit the scope or meaning of the claims.

In accordance with some embodiments of the present invention, an imaging apparatus includes an optical source, an x-y scanner receiving light from the optical source and directing it onto a sample, a detector receiving reflected light from the scanner, and a computer receiving a signal from the detector and providing a 3D data set containing voxels of a sample, the computer further executing instructions for processing the 3D data set, identifying one or more 3D seeds from the 3D data set, performing image processing to obtain characteristics of 3D disruptions from the 3D seeds, generating measurements for the 3D disruptions, and displaying the results of the 3D disruptions.

An image processing method according to some embodiments of the present invention includes acquiring a 3D data set utilizing an OCT system, processing the 3D data set, identifying one or more 3D seeds from the 3D data set, performing image processing to obtain characteristics of 3D disruptions utilizing the 3D seeds, generating measurements for the 3D disruptions, and displaying the results of the 3D disruptions.

These and other embodiments are further discussed below with respect to the following figures.

BRIEF DESCRIPTION OF THE DRAWINGS

FIG. 11 shows exemplary displays of 3D disruption clouds (a) at RPE-fit layer, and (b) at RPE layer.

Where appropriate, elements having the same or similar functions have the same element designation. Figures are not to scale and do not illustrate relative sizes.

DETAILED DESCRIPTION

The aspects and embodiments of the invention disclosed herein relate to a computer-aided detection and measurement system and method to detect and measure the retinal disruption (or elevation), as well as to present the results using the OCT 3D volume data.

In some embodiments, the retinal disruptions are detected by 3D region growing methods with different constraints, such as 3D shape, size, intensity and texture, 3D labeled mask generation, and Intelligent Fundus Image (IFI) construction.

In some embodiments, the 3D disruption seeds for the 3D region growing are obtained by a method which contains retinal layer segmentation of Inner Limiting Membrane (ILM), Inner Plexiform Layer (IPL), Outer Plexiform Layer (OPL), Photoreceptor Inner Segment/Outer Segment (IS/OS), and Retinal Pigment Epithelium (RPE) layers, normal RPE layer construction, IS/OS elevation map construction, Adaptive Seed Search Image (ASSI) construction, and 3D disruption seeds detection from all of the above information as well as the OCT 3D volume data.

In some embodiments, based on the detected disruption, the following quantitative measurements are performed: the number of disruptions, the 3D boundary of each disruption, the size (diameter, area and volume) of each disruption, the distribution of the disruptions, the sum of the disruptions in size in defined regions, e.g. the standard ETDRS (Early Treatment Diabetic Retinopathy Study) sectors, and the change of these measurements over time.

In some embodiments, an interactive Graphical User Interface (GUI) is provided to display the above measurements as well as for changing the intermediate results, e.g. segmented retinal layers, disruptions seeds, and disruption boundaries in 3D, to correct some errors from the auto-method to obtain more accurate results. In some embodiments, progression analysis is performed and the report is provided when multiple datasets are available.

The approaches discussed herein can be implemented on a device for measuring samples using optical coherence tomography (OCT). One such device has been commercially available in the US and internationally by the assignee herein under the trademark RTVue®. A more compact version of such device has also been commercially available in the US and internationally by the assignee herein under the trademark iVue®. Both the RTVue® and the iVue® are frequency domain OCT system with a broadband light source and a spectrometer, and acquire OCT data sets with both high definition scan(s) and lower resolution data cubes within a short period of time capable of clinical interpretation and diagnosis by clinicians. Embodiments described in this disclosure can be applied to any imaging devices and are not limited to the OCT technology discussed above.

A system and method for retinal disruption detection, measurement and presentation using a 3D data set acquired using an OCT scanner is disclosed. Embodiments of the present invention can be utilized to facilitate diagnosis and treatment of retinal diseases with quantitative measurements of disruptions in retina.

Figure 7:
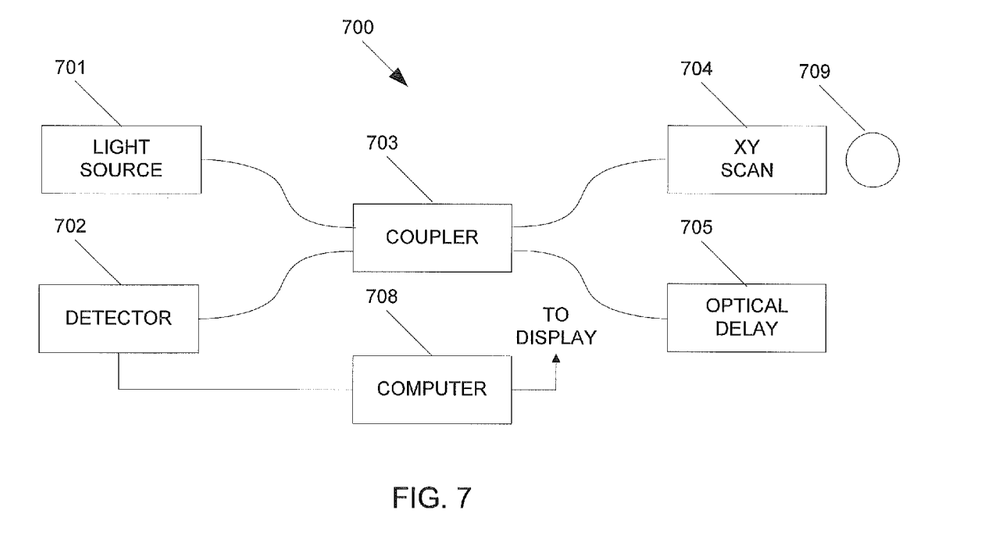
FIG. 7 is a schematic illustration of an Optical Coherence Tomography (OCT) scanner.

FIG. 7 illustrates an example of an OCT imager 700 that can be utilized in 3D retinal disruption detection according to some embodiments of the present invention. OCT imager 700 includes light source 701 supplying light to coupler 703, which directs the light through the sampling arm to XY scan 704 and through the reference arm to optical delay 705. XY scan 704 scans the light across eye 709 and collects the reflected light from eye 709. Light reflected from eye 709 is captured in XY scan 704 and combined with light reflected from optical delay 705 in coupler 703 to generate an interference signal. The interference signal is coupled into detector 702. OCT imager 700 can be a time domain OCT imager, in which case depth (or A-scans) are obtained by scanning optical delay 705, or a Fourier domain imager, in which case detector 702 is a spectrometer that captures the interference signal as a function of wavelength. In either case, the OCT A-scans are captured by computer 708. Collections of A-scans taken along an XY pattern are utilized in computer 708 to generate 3-D OCT data sets. Computer 708 can also be utilized to process the 3-D OCT data sets into 2-D images according to some embodiments of the present invention. Computer 708 can be any device capable of processing data and may include any number of processors or microcontrollers with associated data storage such as memory or fixed storage media and supporting circuitry.

Figure 1:
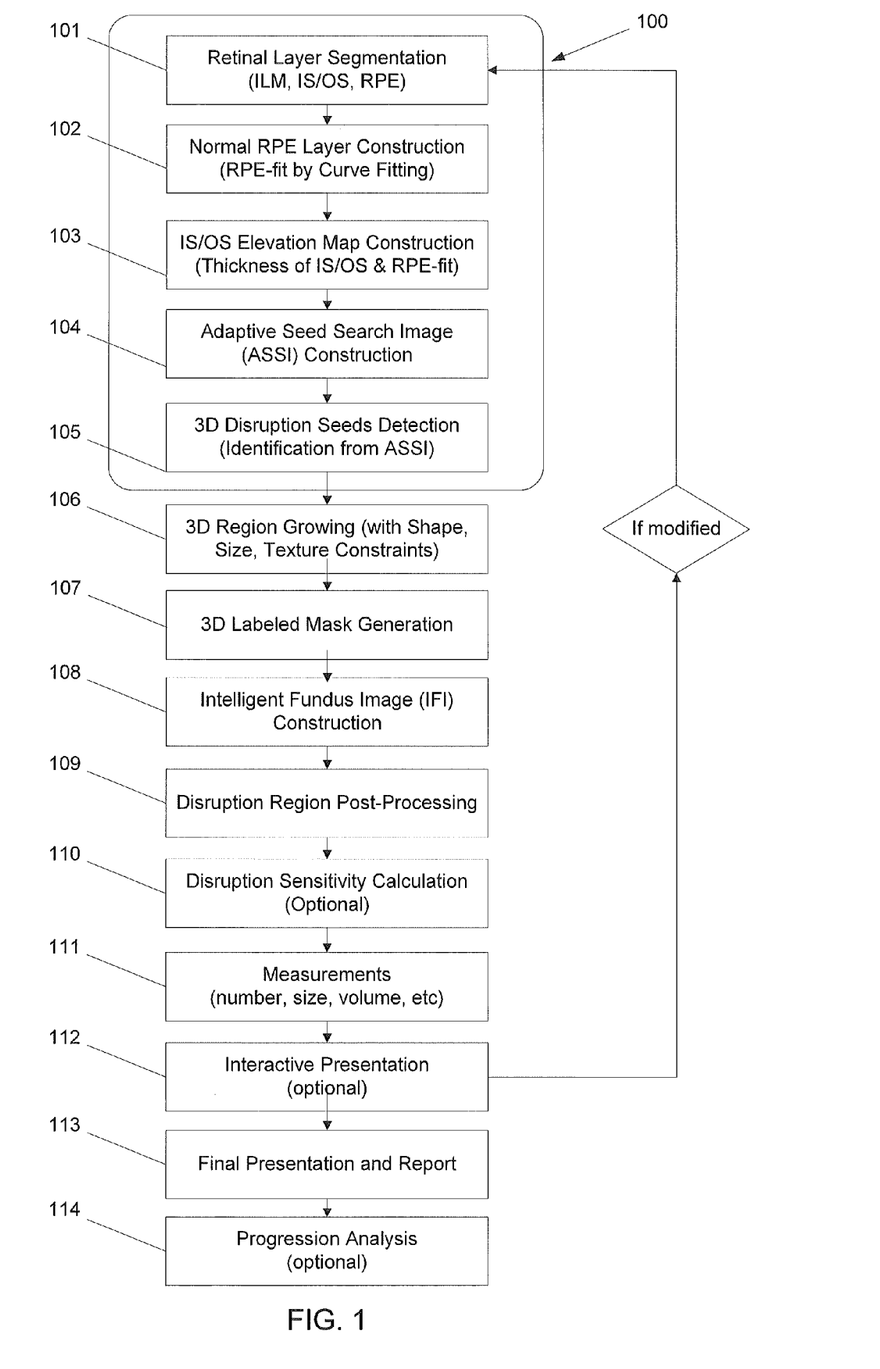
FIG. 1 is an exemplary flowchart of some embodiments of the present invention.

In further illustration, FIG. 1 is an exemplary flowchart of some embodiments of the present invention. In the flowchart illustrated in FIG. 1, there are ten steps of the present retinal disruption detection, measurement and presentation method, namely, 1) 3D disruption seeds detection 100, including five sub-steps 101-105; 2) 3D region growing 106; 3) 3D labeled mask generation 107; 4) Intelligent Fundus Image (IFI) construction 108; 5) disruption region post-processing 109; 6) optional disruption sensitivity calculation 110; 7) measurements assessment 111; 8) optional interactive presentation 112; 9) final presentation and report 113, and 10) optional progression analysis 114.

3D Disruption Seeds Detection

The first step 100 of the flowchart in FIG. 1 is to facilitate the detection of 3D seeds of potential disruptions in the retina, wherein disruptions seeds are detected and identified for subsequent 3D region growing to determine a final 3D disruption volume in the 3D data set. As shown in FIG. 1, step 100 includes five sub-steps for preparing and identifying the seeds and they are described in detailed below.

In sub-step 101, segmentation for different retinal layers of a subject eye, such as Inner Limiting Membrane (ILM), Inner Plexiform Layer (IPL), Outer Plexiform Layer (OPL), Photoreceptor Inner Segment/Outer Segment (PR-IS/OS), Retinal Pigment Epithelium (RPE), choroid boundaries, or other layers of interest, can be performed. Layer segmentation is commonly performed on measurement data acquired using the OCT technology and numerous methods have been used to achieve retinal layer segmentation in OCT data set. Some well-known methods are graph-cut, active contour model (snake), level set theory, and dynamic programming (see for example, J. A. Noble et. al., "Ultrasound Image Segmentation: A Survey", *IEEE Transactions on Medical Imaging*, vol. 25, no. 8, pp. 987-1010, 2006).

The second sub-step 102 is to determine a segmentation curve or surface as a representation of a normal retinal layer, e.g., RPE layer, location by assuming the layer is not disrupted by any disease or pathology; hence, points of disruption suspects on the layer are not considered. For example, this representation of a normal RPE layer location is called a "RPE-fit". In some embodiments, a RPE-fit is assumed to be convex and smooth in local segments and free of disruptions. After excluding the suspected pathological segments, the RPE-fit can be fitted by low order polynomials to represent a normal RPE layer. For instance, second order or third order polynomials are sufficient to achieve an ideal RPE-fit layer. The idea of fitting the RPE surface to the actual RPE from SD-OCT image volume was presented soon after the SD-OCT was developed and methods for line or surface fitting are well-known in the art (see for example, M. Szkulmowski et. Al, "Analysis of posterior retinal layers in spectral optical coherence tomography images of the normal retina and retinal pathologies", Journal of Biomedical Optics 12(4), 2007).

Figure 8:
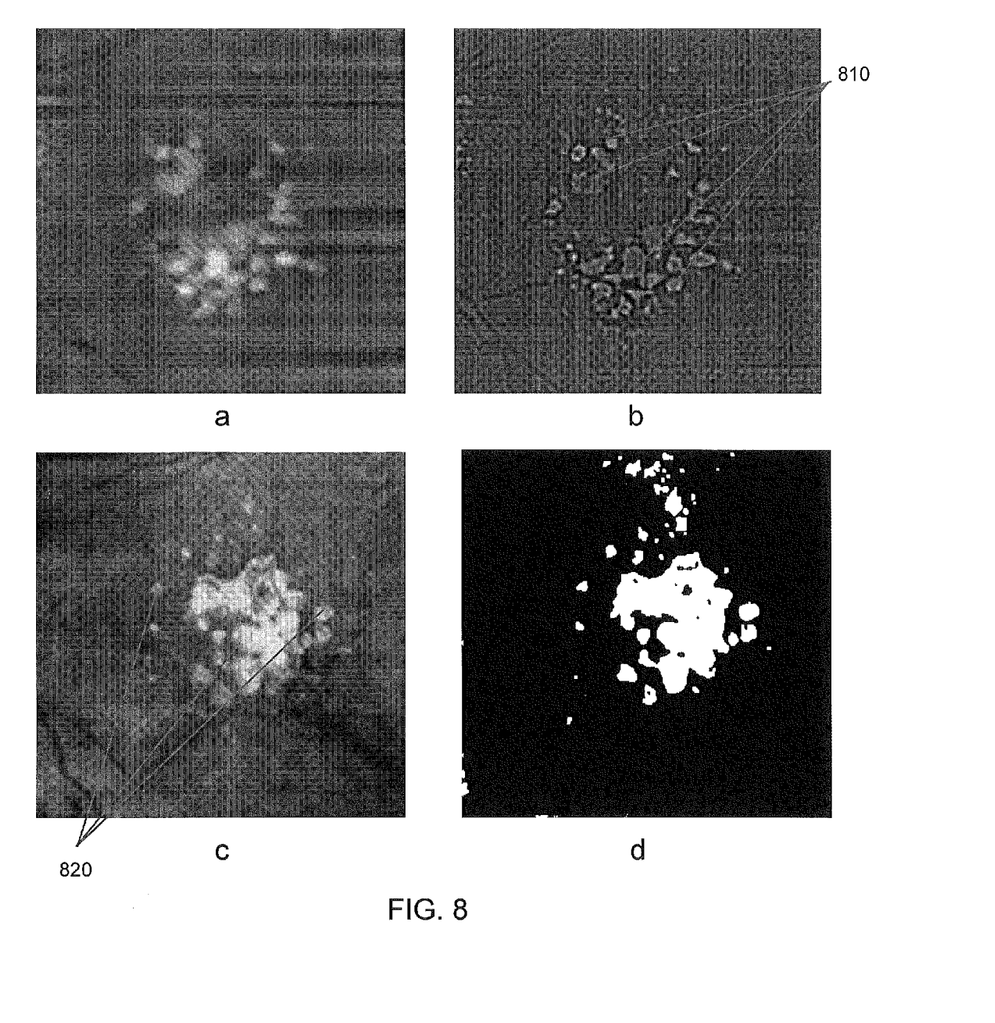
FIG. 8a-d show example images used for 3D disruption seeds generation: (a) Adaptive Seed Search Image (AS SI) using elevation map between inner segment and outer segment (IS/OS) and Retinal Pigment Epithelium (RPE) fit used for 3D disruption seeds generation (b) ASSI to generate drusen/Pigment Epithelium Detachment (PED) 3D disruption seeds; (c) ASSI to generate geographic atrophy 3D disruption seeds; and (d) example 3D disruption seeds for Geographic Atrophy (GA) detection.

The third sub-step 103 is to create an elevation map from the layers of interest. For example, an elevation map of the IS/OS can be created to help identify seed candidates needed for subsequent 3D retinal disruption detection. In some embodiments, the IS/OS segmented layer from step 101 is compared to the RPE-fit generated in step 102 to create an elevation map of IS/OS. FIG. 8a shows an example of an elevation map between IS/OS and RPE-fit that can be used to detect the 3D disruption seeds for drusens with further processing step in accordance with some embodiments of this invention.

The fourth sub-step 104 is to identify seed candidates by evaluating the OCT data distribution for each A-scan between the IS/OS segmented layer step 101 and the RPE-fit layer step 102, or below the RPE-fit layer, depending on the type of disruptions. The evaluation of each A-scan helps confine the search range for the seed candidates and results in an image, called an "Adaptive Seed Search Image" (AS SI). The ASSI enhances the bright regions in the image for seed candidates that can be used to identify potential locations of retina disruptions with further processing.

In some embodiments, sub-step 104 can be performed without performing sub-step 103. For example, to detect GA, the 3D disruption seeds can be detected directly from an ASSI constructed below the RPE-fit layer. The elevation map constructed between IS/OS to RPE fit in step 103 can later be used to further refine the 3D disruption detection constraints and the GA detection results.

FIG. 8b is an example ASSI by performing further image processing, such as edge detection, on an en face image to enhance the disruption regions 810 used in the seeds detection step 105. FIG. 8c is another example ASSI generated by performing further image processing, such as commonly known smoothing filter(s), on an en face image to enhance the disruption regions 820 used to detect a seed in the case of GA disruption. FIG. 8d is an exemplary 2D disruption seeds image generated by locating the regions with value higher than a selected threshold in FIG. 8c.

In some embodiments, local intensity maxima can be extracted from the IS/OS elevation map and the x-y positions of these local maxima can then be considered as the x-y positions of the seed candidates of retinal disruptions for further 3D seed detection in step 105. The local intensity maxima can be detected using commonly used 2D image segmentation algorithm, such as, Otsu adaptive thresholding (Otsu, N, "a threshold selection method from gray-level histograms", IEEE Transactions on Systems, Man, and Cybernetics, Vol. 9, No. 1, pp. 62-66, 1979), a marker controlled watershed transform (Vincent, L and Pierre, S, "Watersheds in Digital Spaces: an efficient algorithm based on immersion simulations", IEEE Transactions on Pattern Analysis and Machine Intelligence, Vol. 13, No. 6, pp. 583-598, 1991.), or a kernel based mean shift clustering (Cheng, Yizong, "Mean shift, mode seeking and clustering", IEEE Transactions on Pattern Analysis and Machine Intelligence, Vol. 17, No. 8, 1995). In some embodiments, the resulting local intensity maxima (brightest points) can be extracted from the ASSI obtained in step 104 and their respective x-y positions of these local maxima can be selected as the 2D seed candidates of 3D retinal disruptions segmentation.

The last sub-step 105 of step 100 is to detect 3D disruption seeds by incorporating the 3D OCT data set, the 2D seed candidates from the elevation map of IS/OS map construction step 103, and/or the 2D seed candidates from the ASSI construction step 104. The previous steps demonstrate the steps to detect the x-y positions of the seed candidates according to an embodiment in the exemplary flowchart in FIG. 1. To obtain seed candidates in a 3D data set, the z positions of the seed candidates need to be determined, for example, by searching the seed candidates from steps 103 and 104 along the A-scan direction with the x-y positions identified in steps 103 and 104. In some embodiments, 3D voxels with the most expected intensity values can be selected to be the 3D seeds. Other common known methods for a person of ordinary skills in the art can be used to identify the z positions using the x-y positions obtained from previous steps. This method effectively determines the x, y and z locations of the 3D seeds to facilitate 3D retinal disruption detection.

Figure 4:
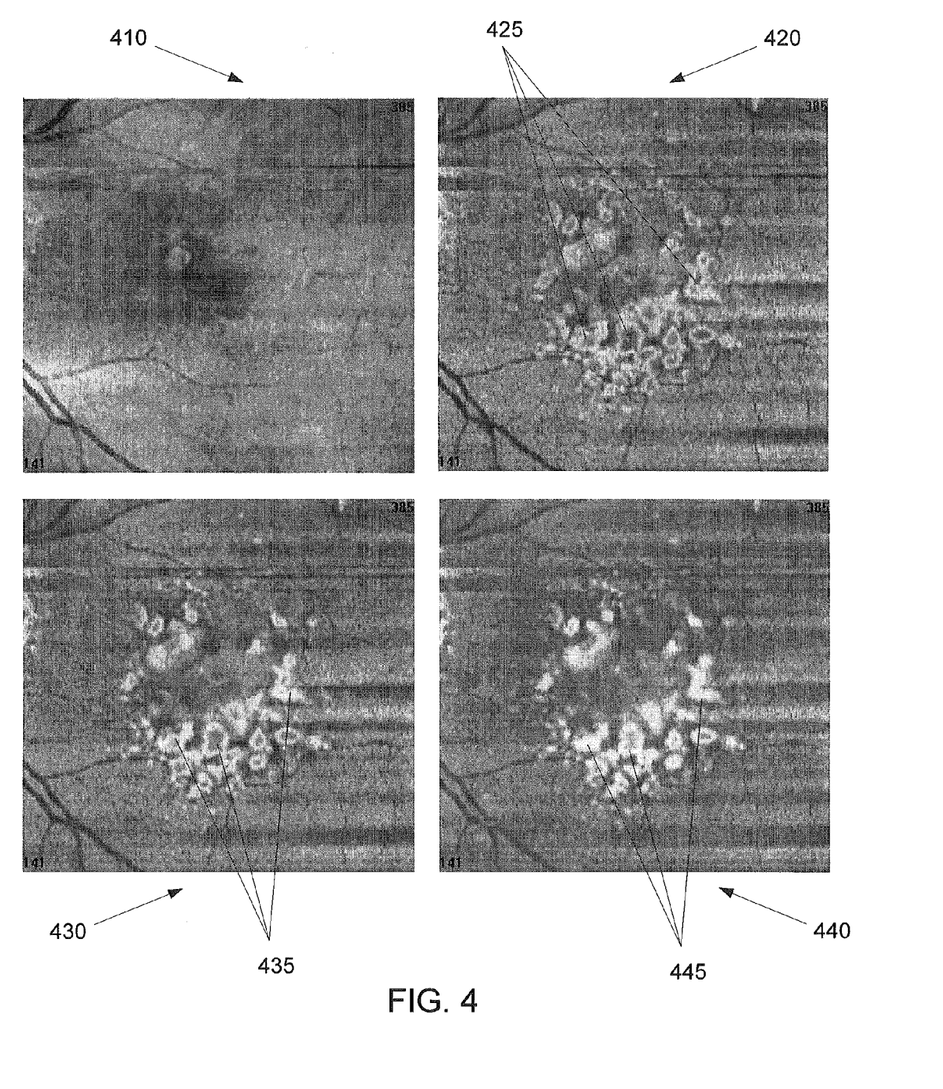
FIG. 4 shows examples of retinal disruptions in en face images with different offsets in the z directions.

FIG. 4 shows examples of retinal disruptions in en face images with different offsets in the z directions. Different techniques have been used to generate en face images (see for example U.S. application Ser. No. 12/909,648). Image 410 shows an en face image obtained from the entire volume of a 3D data set. Image 420 shows an image with 55 um offset from the RPE-fit. Drusens 425 are indicated as the bright spots or brighter boundary surrounding darker area in the image 420. Image 430 is an image from the same 3D data set used to generate image 410 with 54 um offset from the RPE-fit. Drusens 435 are again the bright spots in the image 430. Image 440 is another image using the same 3D data set with 74 um offset from the RPE-fit, with drusens 445 as the bring spots. The characteristics of the drusens 425, 435 and 445 changes from images 420, 430 and 440, with different offset amounts from the RPE-fit. Using this simple approach as shown in FIG. 4, the detection of the actual drusens is likely to be error prone and non-reproducible because the characteristics of drusens in the images are highly dependent on the amount of offsets as shown herein. Therefore, 3D segmentation methods used for 3D retinal disruption detection can significantly improve clinical usefulness of the OCT data.

The embodiments disclosed herein do not simply use 2D segmented surfaces to identify the disruptions directly, but utilize the 2D segmented surfaces as intermediate results to identify local 3D seeds. Based on the local 3D seeds from determined in step 105, 3D region growing techniques can then be applied to detect areas of interest more reliably, especially disruptions of various sizes and locations. Therefore, the accuracy of 2D surface segmentation is less critical as compared to some current methods discussed above.

3D Region Growing

In the exemplary flowchart illustrated in FIG. 1, the next step, step 106, is to perform 3D region growing in the 3D OCT data set. Segmentation methods using 2D region growing are well known in the field (see for example, Adam and Bischof, "Seeded Region Growing," *IEEE Transactions on Pattern Analysis and Machine Intelligence*, vol. 16, pp. 641-647, 1994). 3D region growing in step 106 can be performed using the 3D seeds identified in step 105 with region growing constraints. Some examples of region growing constraints are 3D shape and size determined by clinical understanding of pathologies and image properties of the OCT data set. For instance, many of the retinal disruptions/pathologies, such as, hard and soft drusen, PED, and CNV, form a half-spherical shape above a normal RPE location (RPE-fit) in most cases. Also, image characteristics of the OCT data set, such as area of high reflectivity and salt-pepper texture features, are commonly observed in hard drusen formation. A 3D region growing method utilizing these constraints improves the robustness and accuracy of the region growing process and substantially reduces some commonly known leaking problem often encountered in region growing techniques. In some embodiments, 3D region growing step 106 utilizing the above mentioned constraints using the 3D seeds identified in step 105 is capable of detecting disruptions with diameter as small as 60 um.

Alternatively, in situations where processing time is critical, the 3D disruption regions can be detected using other 3D segmentation techniques other than the 3D region growing method. In some embodiments, 3D segmentation can be performed by interpolating multiple 2D cross-sectional regions at different z distance based on the 3D seeds identified in step 105, similar to piecing together volume using contour map. Some commonly used interpolation methods, such as, linearly, bi-linear, b-spline interpolation can be employed. In some other embodiments, to further reduce process time and computation burden, enhanced 2D retinal disruption can be obtained using the ASSI. For example, ASSI can be constructed from a certain clinically meaningful pre-selected range of z positions, in addition to the adaptive local seed identifications discussed in steps 101 to 105. A 2D region segmentation algorithm (for example, marker-controlled watershed segmentation) can then be applied to generate a 2D counterpart of the 3D labeled disruption mask as in step 107. In some embodiments, for drusen and PED type of disruption, the ASSI can be constructed from 100 um to 30 um above the RPE-fit layer. For Geographic Atrophy (GA) type of disruption, the ASSI can be constructed from 100 um to 400 um below the RPE-fit layer. Additional ASSI image can also be constructed from 100 um above IS/OS layer to IS/OS layer as reference of reflectivity.

3D Labeled Mask Generation

The next step 107 is to label voxels of each of the 3D connected objects segmented using the 3D region growing step 106. For example, the labeling procedure can be as discussed below. First, all voxels filled by the 3D region growing step 106 can be initially assigned a mask value N larger than the maximum allowable number of 3D connected objects identified in step 106 (e.g., N=255, assuming there is less than 255 3D connected objects in the 3D data set); while voxels not filled in step 106 are assigned values of 0. Next, an iterative process can be used to label each of the 3D connected objects with a unique value. The iterative process can have k iterative steps, where 1≤k≤K, and K is the total number of 3D connected objects from step 106. A commonly used flood-fill algorithm can also be applied to a randomly selected voxel having a mask value N to search for all mask voxels connected to this selected voxel. New mask values k will be assigned to these connected voxels having mask values N previously. After this first iteration, k will be incremented (e.g. k=k+1) and the flood-fill algorithm will be applied to another randomly selected voxel having a mask value N to search for voxels connected to this randomly selected voxel. The mask values of these voxels will then be updated to the incremented k value. This iteration process continues and stops at the $K^{th}$ iteration, where there is no more voxel with the mask value initially assigned mask value N. This process labels the K total number of 3D connected objects in the 3D data set to facilitate further processing steps 108-110 and to evaluate subsequent disruption measurements in step 111.

Intelligent Fundus Image (IFI) Construction

Figure 5:
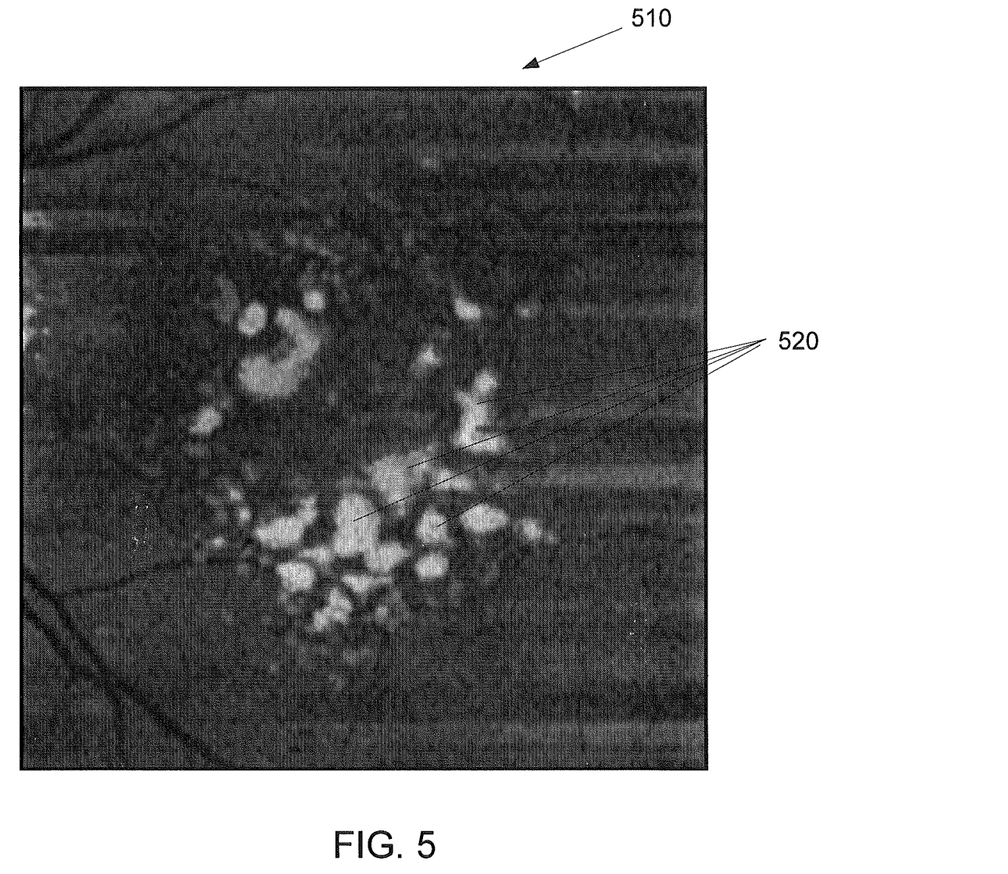
FIG. 5 is an example of an Intelligent Fundus Image (IFI) of some embodiments of the present invention.

Based on the 3D labeled mask inform step 107, an Intelligent Fundus Image (IFI) can be constructed in step 108. 3D data smoothing and enhancement techniques such as nonlinear filtering and histogram equalization can be applied, depending on the application at hand, to one or more specific 3D connected objects to generate the optimal fundus image representation. An example of such IFI is shown in FIG. 5. The IFI image as shown in FIG. 5 resolves the problem of the sensitivity of different arbitrary offset amounts illustrated in FIG. 4. The IFI image as a result of the process described above produces constant and more accurate retinal disruptions characteristics. Image 510 is an image generated from the same 3D data set used for image 410. The characteristics of drusens 520 are more pronounced and can be more clearly identified than drusens 425, 435, or 445 illustrated in images 420, 430, and 440, respectively, of FIG. 4.

Disruption Region Post-Processing

Figure 9:
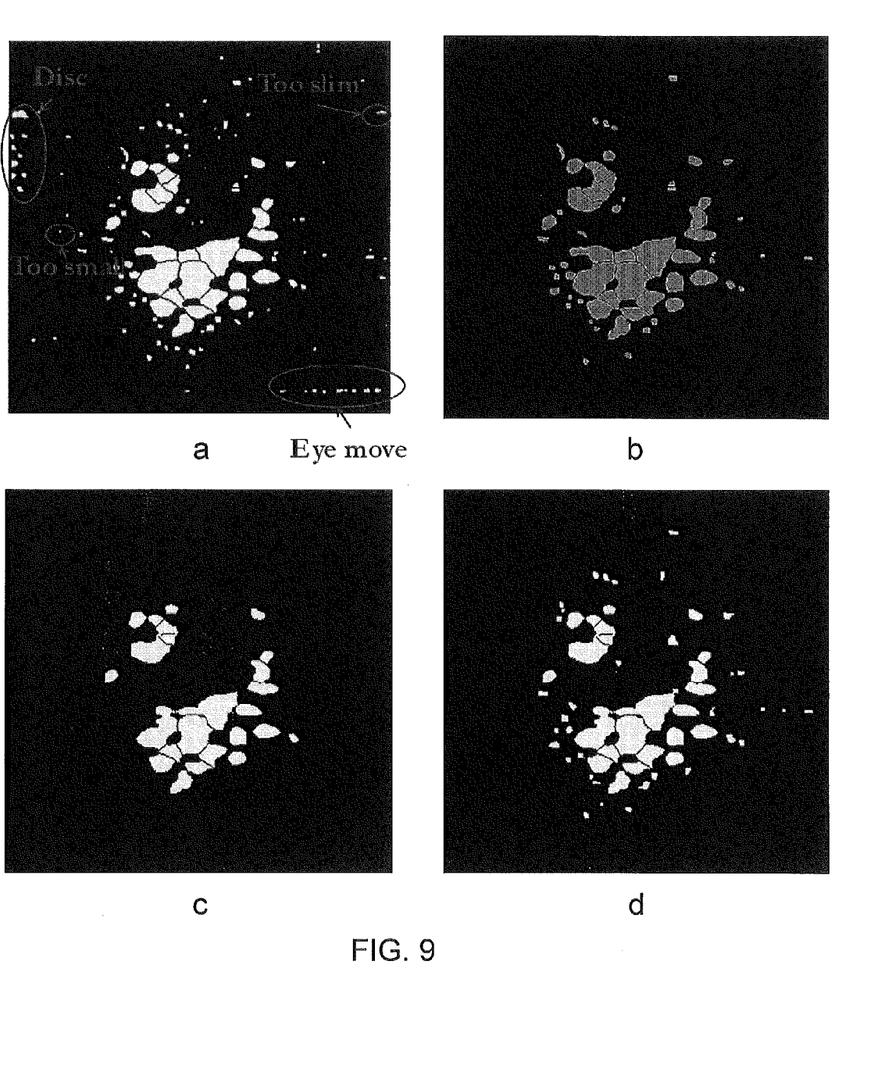
FIG. 9a-d show exemplary images of disruption region: (a) before disruption post processing; (b) after disruption post processing; (c) user defined sensitivity at 0.5; and (d) user defined sensitivity at 1.0.

In some embodiments, disruption region post-processing step 109 can be applied to the disruption labeled mask to remove or minimize the impacts of motion artifacts, such as eye movement during the data acquisition, false positive regions near disc area or due to size and shape, or optical and electronic noise. For example, eye motion can be detected using edge information and histogram distribution of the IFI image. A motion probability map can be constructed and a probability of motion artifacts can then be assigned to each labeled region so that regions with higher motion probability are removed from the disruption image. FIGS. 9a-b show examples of disruption regions before (FIG. 9a) and after (FIG. 9b) the post processing. In FIG. 9b, the artifacts due to eye movement, too small and too slim clusters, and false positive clusters associated with the optic disc area in FIG. 9a were removed. In some embodiments, instead of removing the motion and other artifacts region, the artifacts could be displayed as different shades or colors to make them more distinguishable for easier interpretation.

Disruption Sensitivity Calculation

In accordance with some embodiments of the present invention, an optional step 110 can be implemented to enhance the retinal disruption detection results; a disruption sensitivity metric can be defined and assigned to each disruption region or volume. A sensitivity value can be set in a range reasonable to the user, such as a range of [0.0, 1.0] or [0%, 100%]. User can adjust this parameter to display disruption region or volume at a desire sensitivity level. A high sensitivity value can lead to a larger number of disruptions with smaller sizes to be detected, and vice versa. Alternatively, a user defined fixed sensitivity value can be selected by default. The sensitivity value can be assigned, manually or automatically, using information from the 3D OCT data set, such as, the height of the elevation, the area of the disruption, the volume of the disruption, or combination of these metrics. For instance, if the user wants to visualize large drusens or PED, a lower sensitivity value, such as 0.5 out of 1.0, can be selected. On the contrary, if the user wants to visualize all possible disruptions, a sensitivity value of 1.0 out of 1.0 could be selected. FIG. 9c-d show examples of detected disruption regions with different sensitivity values (sensitivity value at 0.5 and 1.0, respectively).

Disruption Measurements 3D regions of retinal disruptions detection can be achieved as described in steps 100-110 described above. The next step, step 111 of FIG. 1, is to obtain quantified measurements and perform image processing to identify characteristics and properties of the disruptions in a manner to aid in the diagnosis of a disease or a disease state. The measurements of the 3D retinal disruptions are clinically meaningful; and the image processing helps the user to evaluate the identified conditions in a clinically useful manner. In some embodiments of the present invention, the following measurements and image processing can be performed in step 111. Such measurements may include but are not limited to the following:

The number of disruptions;
The 3D boundary of each disruption;
The size (diameter) of each disruption;
The area of each disruption;
The volume of each disruption;
The distribution of the size in the categories of small (<63 um), intermediate (63 um~124 um), large (125 um~249 um), very large (250 um~499 um), super large (>=500 um);
The distribution of the volume, in the same size categories defined above;
The total size of the disruptions in any user specified area;
The total volume of the disruptions in any user specified area;
The total size of the disruptions in the standard ETDRS (Early Treatment Diabetic Retinopathy Study) sectors;
Total circle (6 mm diameter circle);
Center circle (1 mm diameter circle);
Inner ring (1 mm~3 mm ring);
Out ring (3 mm~6 mm ring);
Inner Tempo;
Inner Superior;
Inner Nasal;
Inner Inferior;
Out Tempo;
Outer Superior;
Outer Nasal;
Outer Inferior;
The total volume of the disruptions in the standard ETDRS (Early Treatment Diabetic Retinopathy Study) sectors as defined above; and
Disruption area percentage in the standard ETDRS (Early Treatment Diabetic Retinopathy Study) sectors as defined above.

Figure 10:
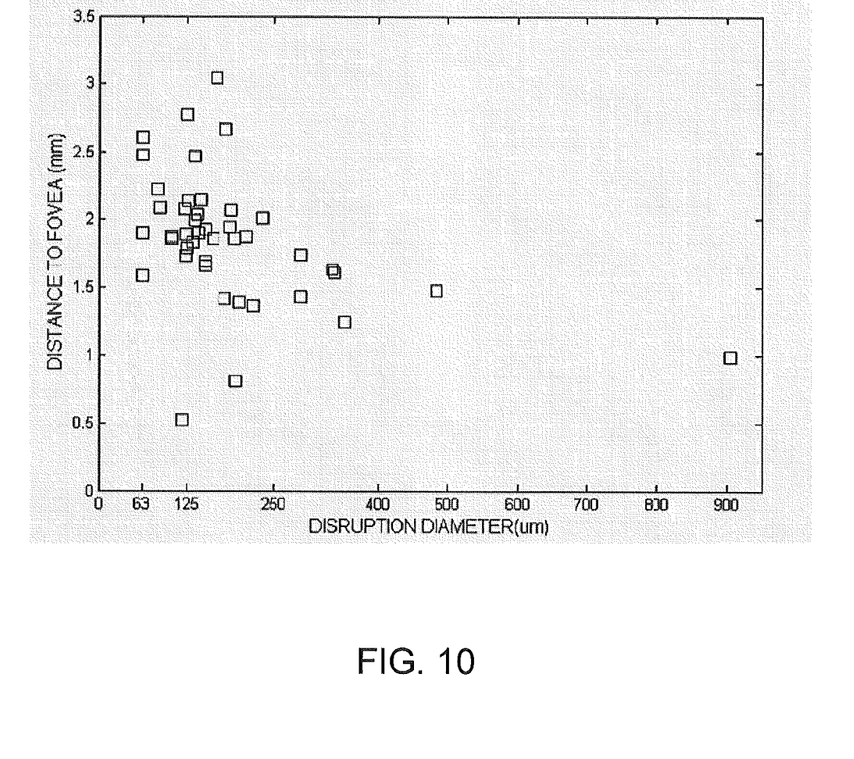
FIG. 10 is an exemplary plot of the relationship between the size of the disruption and its distance to the center of the fovea.

In addition to calculating these numerical measurements, they can be displayed in a clinically meaningful manner. For example, distances of disruption centers to a reference point, such as the fovea, can be calculated and plotted in relation to some measurements, such as diameter, area, or volume of the disruptions. FIG. 10 shows an exemplary plot of the size of the disruption versus its distance to fovea.

Interactive Presentation

An intuitive and user-friendly Graphical User Interface (GUI) providing user interaction with the 3D disruption regions can be employed in some embodiments of the present invention. An interactive GUI presentation step 112 of the 3D retinal disruption segmentation steps 106 to 110 and the measurements performed in step 111 can be incorporated in the exemplary flowchart in FIG. 1. An example of an intuitive and user-friendly user interaction could allow a user to modify the layer segmentation results form step 101 to better identify the region of interest. Another example of such user interaction can allow the user to modify, add, or remove 3D disruption seeds inform step 105 for customized results. Also, such user interaction can allow the user to modify, add, remove, or emphasize the resulting 3D disruption segmentation from step 106. The interactive presentation and GUI allow the user to verify and confirm the detection results to better meet the user's clinical needs. From the retinal layer segmentation to the generation of measurements and image processing of the detected 3D disruption from steps 100-111 can be evaluated again when the user chooses to make a modification through the interactive GUI presentation step 112.

Final Presentation and Report

Figure 2:
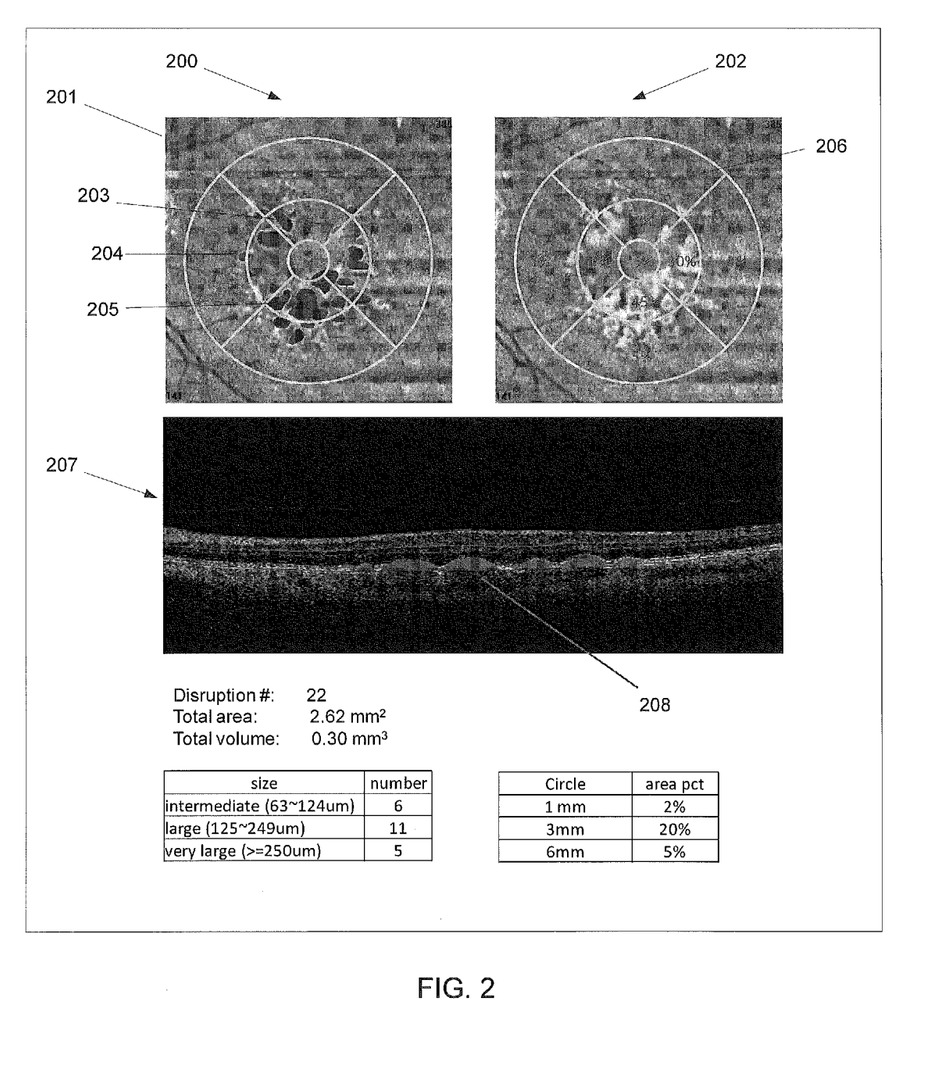
FIG. 2 is an example of a clinically useful presentation scheme for a disruption report.
Figure 3:
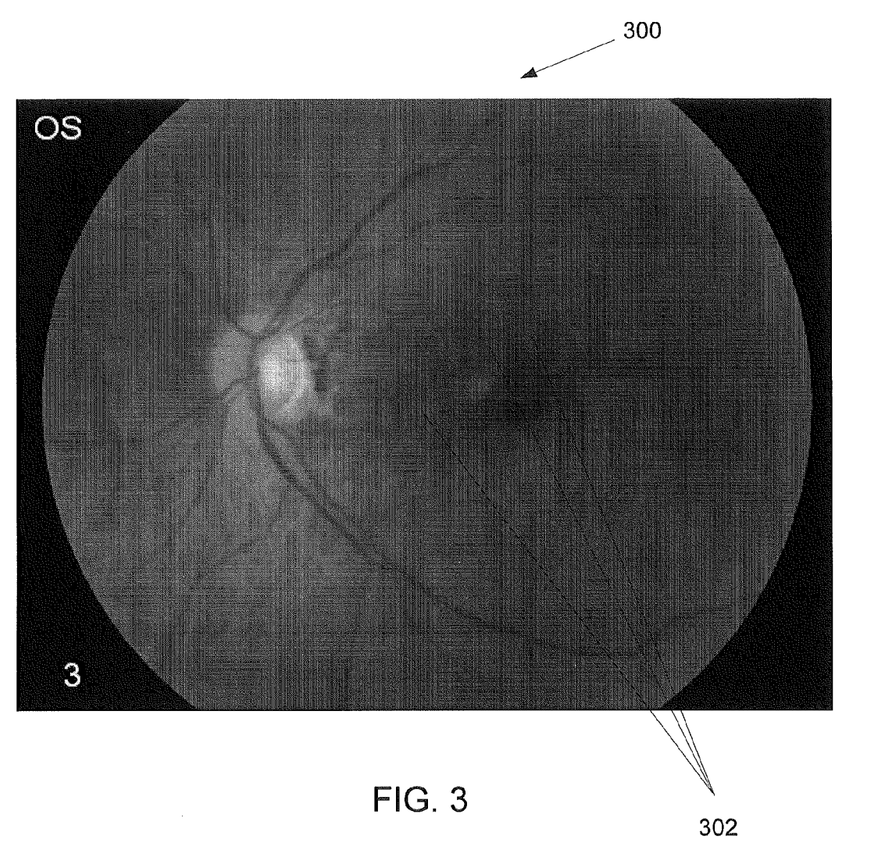
FIG. 3 shows an example of a color fundus photograph with drusen.

After the user has verified and confirmed the 3D retinal disruption results and measurements, a clinically useful detection report can be generated in step 113. FIG. 2 illustrates an example of a clinically useful presentation scheme for a disruption results report. Two IFI 200 and 202 are displayed in this sample report. IFI 200 is an IFI with a ETDRS grid overlay with the detected retinal disruptions highlighted in different colors. A color scheme is used in some embodiments to help easily identify characteristics of the disruptions. Some clinically useful characteristics are area, volume and depth. In this instance in FIG. 2, the color scheme of green 203, purple 204 and red 205 are used to designate the size of the disruption for intermediate, large and very large size, respectively. IFI 202 is an IFI with another ETDRS grid overlay with an area percentage indicated in each of the ETDRS grid region. IFI 202 is a quantitative display to indicate the percentage of area affected in each of the ETDRS region. It is clinically useful to be able to identify the location and concentration of disruption in each of the sensitive ETDRS region. Region 206 is one ETDRS region where 1% in area of the total number of drusens is located. Image 207 is one example of B-scan image where retinal layers are segmented and displayed (first red: ILM, green: IPL, cyan: RPE, second red: RPE-fit). Region 208 is the disruption regions (pink bumps) detected for the corresponding B-scan image. Additionally, some commonly used clinical information can be displayed or integrated in such a report, namely, total disruption number, disruption number for each size category (small, intermediate, large, very large, and super large), total disruption area, disruption area for each ETDRS sectors, total disruption volume, disruption volume for each ETDRS sectors, disruption area percentage for each ETDRS sectors, color ETDRS region by the disruption area percentage, overlay the above colored ETDRS region onto the IFI image 202, overlay the above colored ETDRS region onto the color fundus photograph, and mark the disruption boundaries on to in image, with different color for the boundary to distinguish the size category 200. FIG. 3 shows an example color fundus photograph commonly used by clinicians to identify one form of retinal disruptions (drusens). In photograph 300, drusens 302 are displayed in yellowish color. However, this traditional presentation or report is less clinically useful than the quantitative, objective and more accurate 3D retinal disruption detection method and presentation discussed above.

Figure 11:
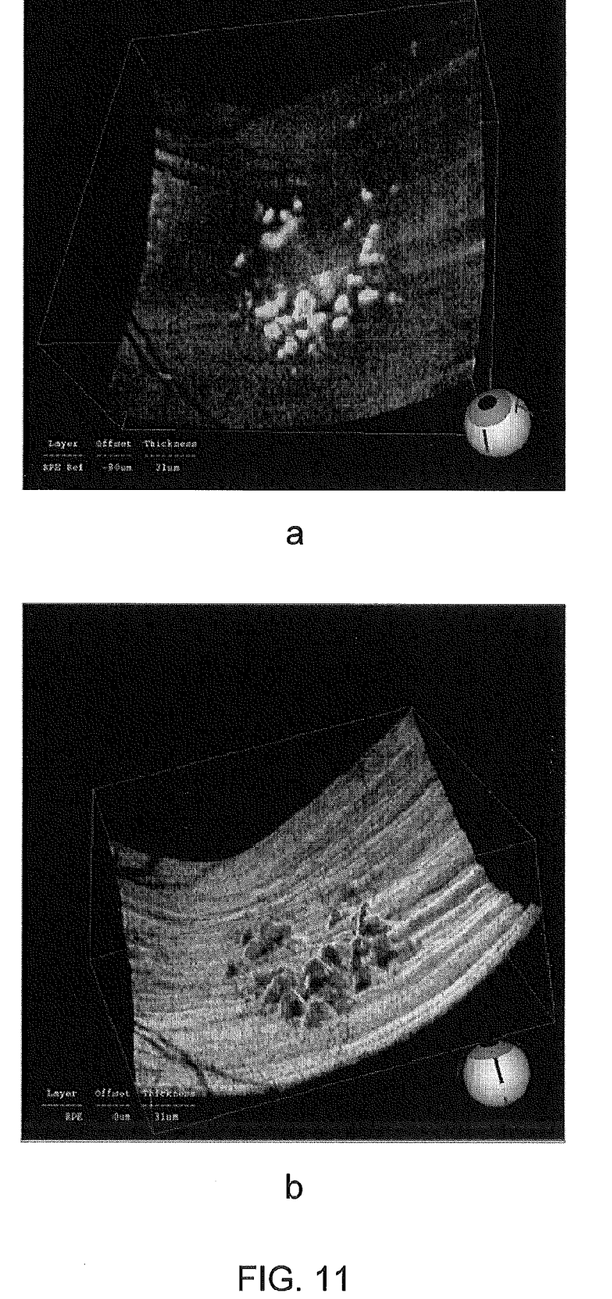

Alternatively, the final presentation of the 3D disruptions can be rendered as "3D disruption clouds" in a 3D display interface. The 3D OCT scan could be displayed in full or at certain layers depending on the user's selection. The 3D disruption clouds can be rendered as pseudo or semi-transparent color volume to present of 3D location and shape. FIG. 11*a* shows an exemplary 3D disruption clouds display at the RPE-fit layer, and FIG. 11*b* shows another example at the RPE layer.

Progression Analysis

Figure 6:
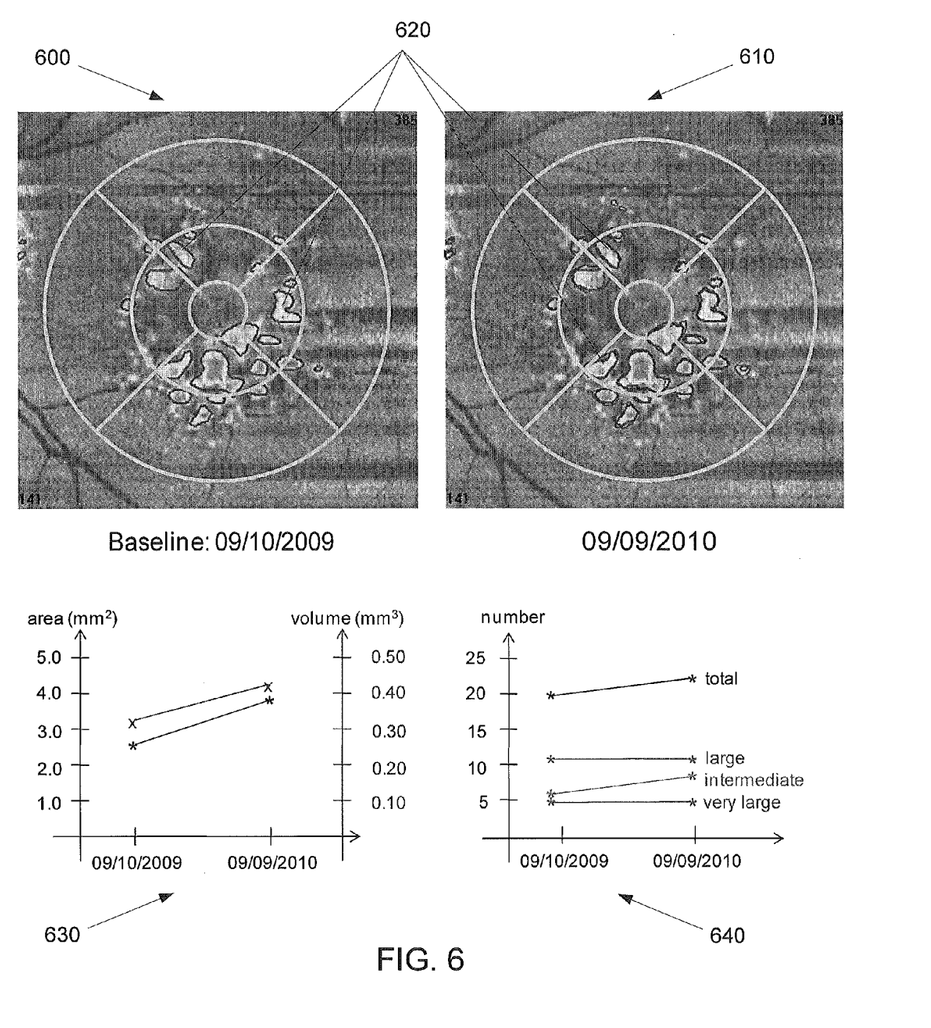
FIG. 6 is an exemplary presentation scheme for a progression report.

In addition to a single clinically useful final report, it is often more advantageous for a clinician to be able to monitor and effectively track a condition or a disease state in the field of ophthalmology. Some embodiments of the present invention include an integrated progression report generated in reporting step 114, which compares and presents clinically useful information from longitudinal exams acquired within or across multiple visits. FIG. 6 is an exemplary presentation scheme for a progression report; it shows an example of a progression analysis for two data sets acquired in two different points in time, points 600 and 610 (retinal disruption 620 segmented with boundaries). The number of longitudinal data sets can be extended from two to a reasonable number that would be clinically meaningful. When multiple datasets are available (often from multiple patient visits), progression analysis can be performed and the progression report can then be generated. When multiple data sets are available, the analysis from steps 100 to 113 of disruption 3D seeds detection will be adapted accordingly to use the multiple datasets. Using multiple dataset can further help validate and enhance robustness of the 3D disruption detection method, especially when the disease state does not change significantly between visits. Some common and clinically meaningful display and representation of measurements can be used in the progression report, for example, change in total disruption number, change in disruption number for each size category, change in disruption area, change in disruption area for each ETDRS sectors, change in disruption volume, change in disruption area percentage for each ETDRS sectors, and change in the disruption region, overlaid onto IFI images, with different colors for the disruption areas only in one data, and disruption areas in both datasets. Examples of some of these useful information are shown in graphs 630 and 640. A similar report can be created for other disruption presentation and measurement discussed above by a person with ordinary skill in the art within the scope of the present invention.

As is demonstrated from the analysis of data obtained from each of the prior art techniques, none of them provide a complete, reliable, or accurate analysis of the 3D retinal disruption. Each fails to reliably determine one or more measurement or segmentation in an accurate and reproducible manner.

The above examples are provided in order to demonstrate and further illustrate certain embodiments and aspects of the present invention and are not to be construed as limiting the scope thereof. In the description above, reference is made primarily to the eye as the object. This has to be understood as merely a way to help the description and not as a restriction of the application of the present invention. As such, where the term "eye" is used, a more general transparent and scattering object or organ may be sought instead. Similarly, embodiments described herein use drusen and RPE-disruption as example demonstration and the same embodiments can be applied to retinal disruption generally. Although various embodiments that incorporate the teachings of the present invention have been illustrated and described in detail herein, a person of ordinary skill in the art can readily device other various embodiments that incorporate the teachings of this subject invention.

We claim:

1. An imaging apparatus, comprising:
an optical source;
an x-y scanner receiving light from the optical source and directing it onto a sample;
a detector receiving reflected light from the scanner; and
a computer receiving a signal from the detector and executing code stored in a memory, the code providing instructions for
providing a 3D data set containing voxels of a sample,
dentifying one or more 3D seeds from the 3D data set by using an adaptive seed search image (ASSI),
obtaining characteristics of 3D disruptions based on the 3D seeds,
generating measurements for the 3D disruptions, and
displaying the results of the 3D disruptions.

2. The apparatus of claim 1, wherein identifying one or more 3D seeds from the 3D data set includes:
segmenting at least one retinal layer in the 3D data set to obtain one or more segmented retinal layers;
generating a notinal Retinal Pigment Epithelium (RPE) layer from the at least one retinal layer in the 3D data set to obtain a RPE fit surface; and
calculating a distance between points on the one or more segmented retinal layers to points on the RPE fit surface to obtain at least one elevation map.

3. The apparatus of claim 2, further including reducing the 3D data set between the one or more segmented retinal layers into a 2D representation to obtain an en face image.

4. The apparatus of claim 3, wherein the en face image is processed by applying an image processing filter to obtain the ASSI, the processing filter being chosen from a set of filters consisting of an edge detection filter, a smoothing filter, and the combination thereof.

5. The apparatus of claim 3, wherein the ASSI can be generated by combining information of the elevation map and the en face image.

6. The apparatus of claim 2, wherein identifying one or more 3D seeds from the 3D data set includes a 3D segmentation computation.

7. The apparatus of claim 6, wherein the 3D segmentation computation includes a 3D volume construction method by interpolating two or more 2D cross-sectional contour images from the 3D dataset.

8. The apparatus of claim 6, wherein the 3D segmentation computation includes a 3D region growing method using region growing constraints.

9. The apparatus of claim 1, wherein the ASSI is an elevation map.

10. The apparatus of claim 1, wherein generating measurements for the 3D disruptions is interactive.

11. The apparatus of claim 1, wherein displaying the results of the 3D disruptions includes providing plots of one or more 3D disruption characteristics in relation to at least one anatomical feature of an eye.

12. The apparatus of claim 1, further including a progression analysis to evaluate and display 3D disruption results from the 3D data set obtained from different points in time.

13. The apparatus of claim 1, further including a 3D display of 3D disruption clouds overlaying a segmented layer of interest in a 3D display interface.

14. An image processing method, comprising:
acquiring a 3D data set containing voxels of a sample from an Optical Coherent Tomography (OCT) system;
identifying one or more 3D seeds from the 3D data set by using an adaptive seed search image (ASSI);
obtaining characteristics of 3D disruptions based on the 3D seeds;
generating measurements for the 3D disruptions; and
displaying results of the 3D disruptions.

15. The method of claim 14, wherein identifying one or more 3D seeds from the 3D data set includes:
segmenting at least one retinal layer in the 3D data set to obtain one or more segmented retinal layers;
generating a normal Retinal Pigment Epithelium (RPE) layer from the at least one retinal layer in the 3D data set to obtain a RPE fit surface; and
calculating a distance between points on the one or more segmented retinal layers to points on the RPE fit surface to obtain at least one elevation map.

16. The method of claim 15, further including reducing the 3D data set between the one or more segmented retinal layers into a 2D representation to obtain an en face image.

17. The method of claim 16, wherein the en face image is processed by applying an image processing filter to obtain the ASSI, the processing filter being chosen from a set of filters consisting of an edge detection filter, a smoothing filter, and the combination thereof.

18. The method of claim 16, wherein the ASSI can be generated by combining information of the elevation map and the en face image.

19. The method of claim 15, wherein identifying one or more 3D seeds from the 3D data set includes a 3D segmentation computation.

20. The method of claim 19, wherein the 3D segmentation computation includes a 3D volume construction method by interpolating two or more 2D cross-sectional contour images from the 3D dataset.

21. The method of claim 19, wherein the 3D segmentation computation includes a 3D region growing method using region growing constraints.

22. The method of claim 14, wherein the ASSI is an elevation map.

23. The method of claim 14, wherein generating measurements for the 3D disruptions is interactive.

24. The method of claim 14, wherein displaying the results of the 3D disruptions includes providing plots of one or more 3D disruption characteristics in relation to at least one anatomical feature of an eye.

25. The method of claim 14, further including a progression analysis to evaluate and display 3D disruption results from the 3D data set obtained from different points in time.

26. The method of claim 14, further including a 3D display of 3D disruption clouds overlaying a segmented layer of interest in a 3D display interface.

* * * * *